United States Patent
Wu et al.

(10) Patent No.: US 9,586,886 B1
(45) Date of Patent: Mar. 7, 2017

(54) METHOD OF FABRICATING FATTY ACIDS THROUGH TRANSACYLATION

(71) Applicant: CPC Corporation, Taiwan, Taipei (TW)

(72) Inventors: Jung-Chung Wu, Chiayi (TW); Ming-Yu Huang, Chiayi (TW); Jann-Chen Lin, Chiayi (TW); Yih-Ping Wang, Chiayi (TW)

(73) Assignee: CPC CORPORATION, TAIWAN, Taipei (TW)

( * ) Notice: Subject to any disclaimer, the term of this patent is extended or adjusted under 35 U.S.C. 154(b) by 0 days.

(21) Appl. No.: 15/133,418

(22) Filed: Apr. 20, 2016

(51) Int. Cl.
- *C07C 67/29* (2006.01)
- *C07C 67/04* (2006.01)
- *C07C 51/00* (2006.01)
- *C07C 67/08* (2006.01)
- *C07C 67/02* (2006.01)

(52) U.S. Cl.
CPC ............ *C07C 67/29* (2013.01); *C07C 51/00* (2013.01); *C07C 67/02* (2013.01); *C07C 67/04* (2013.01); *C07C 67/08* (2013.01)

(58) Field of Classification Search
None
See application file for complete search history.

(56) References Cited

U.S. PATENT DOCUMENTS

| 7,208,605 | B2* | 4/2007 | Davis, Jr. ............... C07C 45/46 548/110 |
| 2011/0184207 | A1* | 7/2011 | Wu .................... C07C 67/08 560/186 |

(Continued)

FOREIGN PATENT DOCUMENTS

CN  102994173 A  * 3/2013  ............ B01J 31/02

OTHER PUBLICATIONS

CN 102994173 (A), Liu Shiwei et al., Method for preparing biodiesel and co-producing triacetin, 2013, English translation, 10 pages.*

(Continued)

*Primary Examiner* — Yate K Cutliff
(74) *Attorney, Agent, or Firm* — Jackson IPG PLLC; Demian K. Jackson

(57) ABSTRACT

Fatty acids are produced through transacylation. An organic nitrogen-containing compound is reacted with alkyl sultone to generate a white solid of a zwitterionic compound. After being purified and dried, the white solid is powdered to be reacted with a Bronsted strong acid for obtaining a clear viscous water-based acidic ionic liquid (IL) as a catalyst used used to effectively process transacylation between oil and acetic acid (HOAc) for fabricating fatty acid (FFA) and glycerol triacetate (GTA). Therein, unsaturated fatty acid is simultaneously processed through addition acetoxylation to obtain stabilized acetoxy fatty acid (AFFA). After, HOAc is recycled through vacuuming. Then, the product and the IL are stratified. The product at upper layer is taken out. The IL at lower layer can be recycled for processing transacylation and addition acetoxylation repeatedly. Therein, fatty acids including the stabilized AFFA are obtained from the product after taking out GTA through vacuum distillation.

14 Claims, 3 Drawing Sheets

(56) References Cited

U.S. PATENT DOCUMENTS

2011/0245522 A1* 10/2011 Wu .................. C11C 3/003
554/161
2013/0109882 A1* 5/2013 Wu .................. B01J 31/0279
560/263

OTHER PUBLICATIONS

Xing, H., et al., Novel Bronsed-Acidic ionic liquids for esterification, 2005, Ind. ENg. Chem. Res., vol. 44, No. 11, pp. 4147-4150.*
Liu, S., et al., Synghesis of glycerol triacetate using a bronstead-Lewis acidic ionic liquid as the catalyst, 2015, J. Am. Chem Soc., vol. 92, pp. 1253-1258.*
Black. L.T., et al., Acetoxylation of methyl oleate with a resin catalyst, 1967, The journal of the american oil chemists' society, vol. 44, No. 5, pp. 310-312.*

* cited by examiner

METHOD OF FABRICATING FATTY ACIDS THROUGH TRANSACYLATION

TECHNICAL FIELD OF THE INVENTION

The present invention relates to fabricating fatty acids; more particularly, relates to a green catalytic process of using an acidic ionic liquid (IL) as a catalyst to simultaneously process transacylation of oil and addition acetoxylation of unsaturated fatty acid for generating stabilized fatty acids.

DESCRIPTION OF THE RELATED ARTS

Globally, the annual yield of animal or vegetable oils & fats is about 2 million tons. The vegetable oil mainly includes soybean oil, palm oil, sunflower oil, rapeseed oil and is mainly used as a cooking oil for fried and deep-fried food. The fats may be acidified and deteriorated when being used at high temperature. If the acid value exceeds a certain level, an oil is no longer available and becomes a so-called waste edible oil. The global annual yield of waste edible oil is quite considerable. Thus, how to effectively use waste edible oil catches global attention for researches. In general, after processing transesterification with methanol, fatty acid methyl ester (FAME) is generated to be used as a bio-diesel additive for dealing with the problem of carbon emission due to excessive burning of fossil fuel. Carbon emission would worsen greenhouse effect, global warming and climate change. Besides, FAME obtained after transesterification can be processed through epoxidation to obtain epoxy fatty acid methyl ester to be used as a low-molecular-weight plasticizer. Because the transesterification process produces nearly 10% glycerol, how to effectively use glycerol is also a considerable factor on economic assessment for the transesterification process. Although the transesterification process has a variety of improved technologies, the commercialize processes are still mainly those using liquid-phase alkali catalysts. However, those processes require more stringent qualities over feedstocks; and, yet, the problems of waste acid and waste water generated during the processes have to be overcome.

Nowadays, the biodiesel (FAME) used is apt to become moldy. Acylated sterol glucoside (ASG) in vegetable oil may be turned into sterol glucoside (SG) after transesterification. Because SG is not dissolved in biodiesel and has very little content, it is difficult to be removed through a refining process and may be slowly crystallized and precipitated to cause congestion to automotive tubing. Moreover, after refining, saturated succinylated monoglycerides (SMG) may be also precipitated to result in tubing congestion. Hence, improvement must be made in fields of source material selection and the refining process for successfully promoting the use of FAME as biodiesel. As shown in some reports, soybean oil and palm oil contain more ASG and SG while grape seed oil is relatively less.

To overcome these problems on using FAME as biodiesel, another method is considered. Waste edible oil can be processed through transacylation and addition acetoxylation with acetic acid (HOAc) to obtain stabilized acetoxy fatty acid (AFFA) and glycerol triacetate (GTA). Such stabilized fatty acids can be reacted with suitable alcohols for esterification to produce green rubber softening oil, non-toxic plasticizer, biomass fat, etc. GTA itself can be used as a non-toxic plasticizer having a low molecular weight. Both processes of esterification and transacylation use strong acidic catalysts, such as sulfuric acid ($H_2SO_4$), hydrofluoric acid (HF), p-toluenesulfonic acid (p-$CH_3$—$C_6H_4$—$SO_3H$ or P-TSA), trifluoromethane sulfonic acid ($CF_3SO_3H$ or TFMSA), heteropoly acid (HPA), etc. However, although the liquid acidic catalysts can be effectively used for esterification and transacylation, the whole processes still have to deal with issues like waste acid.

Hence, the prior arts do not fulfill all users' requests on actual use.

SUMMARY OF THE INVENTION

The main purpose of the present invention is that, by using a water-based acidic IL as a catalyst, an oil is processed through transacylation and addition acetoxylation to generate AFFA and GTA, where problems of product stratification, waste acid treatment and equipment corrosion are solved; and the yields of products generated through transacylation and addition acetoxylation are improved.

Another purpose of the present invention is to directly and effectively convert waste edible oil or epoxy oil into AFFA and GTA; and non-edible oil (vegetable waste acid), like jatropha oil, castor oil, high-acid algae oil, pongamia oil, etc., into high-price environmentally-friendly non-toxic biomass ester products.

To achieve the above purposes, the present invention is a method of fabricating fatty acids through transacylation, comprising steps of: (a) reacting an organic nitrogen-containing compound with an alkyl sultone to obtain a white solid of a zwitterionic compound; after being purified and dried, forming a powder of the white solid to be reacted with a Bronsted strong acid in HOAc to obtain a clear viscous water-based acidic IL, where a mole ratio of the Bronsted strong acid to the zwitterionic compound is 1.0~3.0; (b) adding a mixture of an oil (triglyceride, TG) and HOAc in the IL; using the oil and HOAc as a reactant feedstock and the IL as a catalyst to process transacylation and addition acetoxylation under reaction conditions of a temperature of 50~150 celsius degrees (° C.) and a reaction time of 1~72 hours (hr), where a molar ratio of the IL to the oil is 0.2~2.0 and a molar ratio of HOAc to the oil (HOAc/TG) in the reactant feedstock is 5~80; and (c) after reactions, recycling HOAc through vacuuming by heating under a reduced pressure; stratifying a product and the IL by staying still; taking out the product at upper layer and leaving the IL at lower layer to be recycled to repeatedly process transacylation and addition acetoxylation with the reactant feedstock added; and obtaining fatty acids including a stabilized AFFA from the product at the upper layer after taking out GTA through vacuum distillation. Accordingly, a novel method of fabricating fatty acids through transacylation is obtained.

BRIEF DESCRIPTION OF THE DRAWINGS

The present invention will be better understood from the following detailed description of the preferred embodiment according to the present invention, taken in conjunction with the accompanying drawings, in which.

DESCRIPTION OF THE PREFERRED EMBODIMENT

The following description of the preferred embodiment is provided to understand the features and the structures of the present invention.

Figure 1:
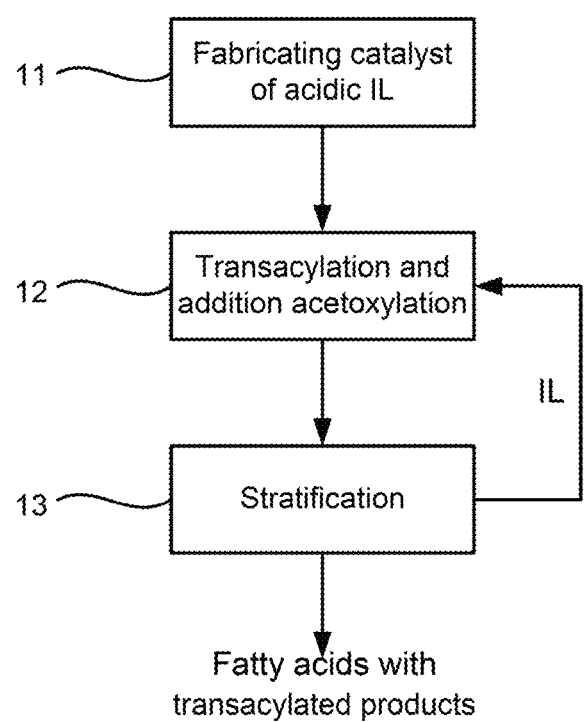
FIG. 1 is the flow view showing the preferred embodiment according to the present invention.

Please refer to FIG. 1, which is a flow view showing a preferred embodiment according to the present invention. As shown in the figure, the present invention is a method of fabricating fatty acids through transacylation. A water-based acidic IL is used as a catalyst to process transacylation of oil and addition acetoxylation of unsaturated fatty acid for producing fatty acids, including a stabilized acetoxy fatty acid (AFFA) and glycerol triacetate (GTA). The present invention comprises the following steps:

(a) Fabricating catalyst of acidic IL 11: At first, an organic nitrogen-containing compound of an alkylimidazole, an alkylpyridine or an alkylamine (e.g. N-Butyl imidazole) is reacted with an alkyl sultone (e.g. 1,3-Propane sultone or 1,4-Butane sultone) to generate a white solid of a zwitterionic compound. After being dried and purified with ether, a white solid powder is obtained. Then, the white solid powder is mixed with a Bronsted strong acid (e.g. sulfuric acid ($H_2SO_4$), an alkyl sulfonic acid ($R-SO_3H$) and heteropoly acid (HPA)) to be stirred for reactions in acetic acid (HOAc) for 1 hour (hr) at a temperature of 80~105 celsius degrees (° C.). Thus, a clear viscous water-based acidic IL, i.e. Bronsted acid IL, is obtained, where a mole ratio of the Bronsted strong acid to the zwitterionic compound is 1.0~3.0

(b) Transacylation and addition acetoxylation 12: A mixture of an oil (triglyceride, TG) and HOAc is added in the IL. The mixture of the oil and HOAc is used as a reactant feedstock and the IL is used as a catalyst for processing transacylation and addition acetoxylation under reaction conditions of a reaction temperature of 50~150° C. and a reaction time of 1~72 hrs to produce fatty acids, including a stabilized AFFA and GTA. Therein, a molar ratio of the IL to the oil is 0.2~2.0; a molar ratio of HOAc to the oil (HOAc/TG) in the reactant feedstock is 5~80; and, the reaction temperature is a little higher on the occasion that HOAc is recycled or the reactions are processed in a closed reaction system.

(c) Stratification 13: After the reactions, HOAc is recycled through vacuuming by heating under a reduced pressure. A product and the IL are stratified by staying still. The product is located at the upper layer and the IL is located at the lower layer. The fatty acids, including GTA and the stabilized AFFA, can be obtained from the product at the upper layer through vacuum distillation; and, the IL at the lower layer can be processed to be re-added with the reactant feedstock for processing transacylation and addition acetoxylation repeatedly.

The oil can be a waste edible oil, an epoxy oil or an energy crop oil. The energy crop oil can be a non-edible oil (vegetable waste acid), like jatropha oil, castor oil, high-acid algae oil, pongamia oil, etc. The present invention can directly convert waste edible oil or epoxy oil into AFFA and GTA; and effectively convert non-edible oil into high-price environmentally-friendly non-toxic biomass ester products.

The alkyl sulfonic acid mentioned as the Bronsted strong acid can be fluorosulfuric acid ($FSO_3H$, FS), trifluoromethane sulfonic acid ($CF_3SO_3H$, TFMSA) or p-toluenesulfonic acid (p-$CH_3-C_6H_4-SO_3H$, P-TSA).

The HPA mentioned as the Bronsted strong acid can be phosphotungstic acid ($H_3PW_{12}O_{40}$), phosphomolybdic acid ($H_3PMo_{12}O_{40}$), silicotungstic acid ($H_4SiW_{12}O_{40}$) and silicomolybdic acid ($H_4SiMo_{12}O_{40}$); and the HPA must be calcined at a temperature of 100~500° C. at first to remove a part of crystal water.

Thus, a novel method of fabricating fatty acids through transacylation is obtained.

The present invention uses the Bronsted acidic IL as a catalyst to effectively process transacylation of the oil and addition acetoxylation of unsaturated fatty acid for producing AFFA and GTA. Therein, excess amount of HOAc is required to obtain a high rate of conversion for transacylation having the following formula:

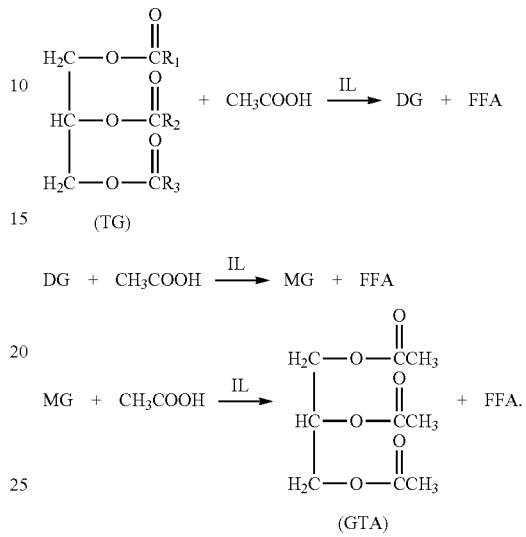

In the above formula, TG is the oil, DG is diglyceride, MG is monoglyceride and FFA is fatty acid, where DG, MG and FFA have the following formula:

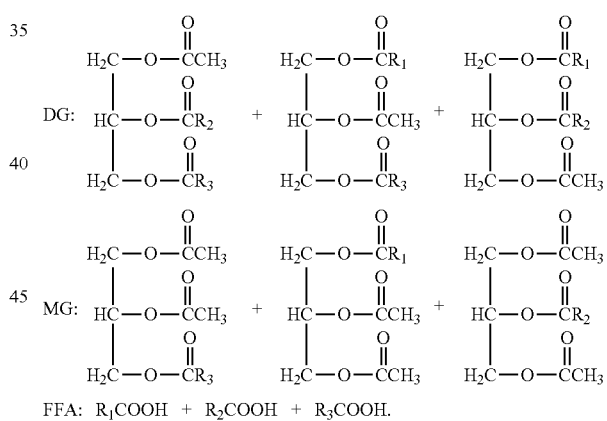

In the above formula, each of $R_1$, $R_2$ and $R_3$ has a formula of $C_nH_{2n+1}$, $C_nH_{2n-1}$ or $C_nH_{2n-3}$, where n is 12~18.

If the fatty acid contains an unsaturated double bond, addition acetoxylation will be processed with transacylation simultaneously for compositing the stabilized AFFA, whose formula is as follows:

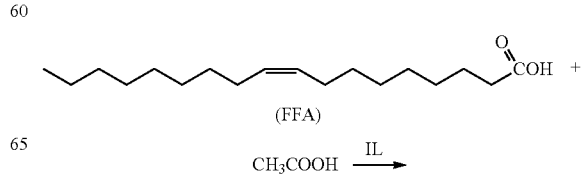

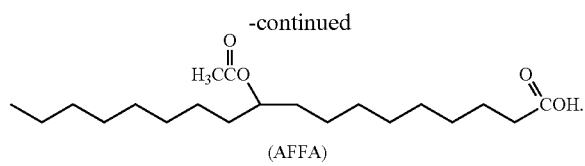

(AFFA)

Conclusively, the reaction is summed as follows:

TG+HOAc→DG+MG+FFA+AFFA+GTA.

In the above formula, AFFA is the stabilized AFFA. If the oil (TG) is completely transacylated (neither DG nor MG is found in the product), a theoretical molar percents (mole %) of the fatty acids (FFA+AFFA) and GTA are 75 mole % and 25 mole %, respectively.

The present invention uses the Bronsted acidic IL to process transacylation and addition acetoxylation under certain conditions. After the reactions, stratification is used to obtain fatty acids and an ester product. After being separated from the IL and removed, HOAc can be recycled for processing transacylation and addition acetoxylation repeatedly.

The acidic IL used in the present invention is mainly obtained by reacting a sulfo-group-containing zwitterionic compound with sulfuric acid. Therein, the anion is $[HSO_4]^-$; the zwitterionic compound can be an imidazole one, a pyridine one or an alkylamine one; and, the zwitterionic compound has formula as follows:

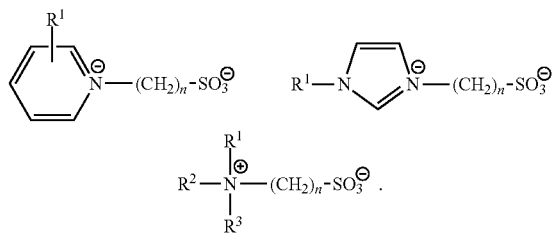

In the above formula, the alkyl group ($R_1$, $R_2$ and $R_3$) in the nitrogen-containing compound (i.e. alkyl imidazole, alkyl pyridine or alkylamine) has a formula of $C_mH_{2m+1}$, where m is 1~18 and n is 3~6.

Figure 2:
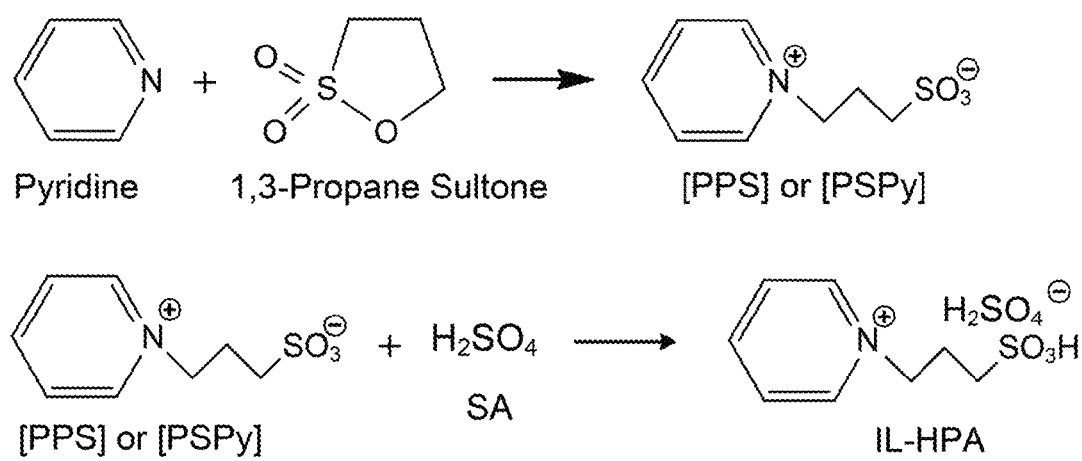
FIG. 2 is the view showing the reactions of fabricating the ionic liquid (IL)
Figure 3:
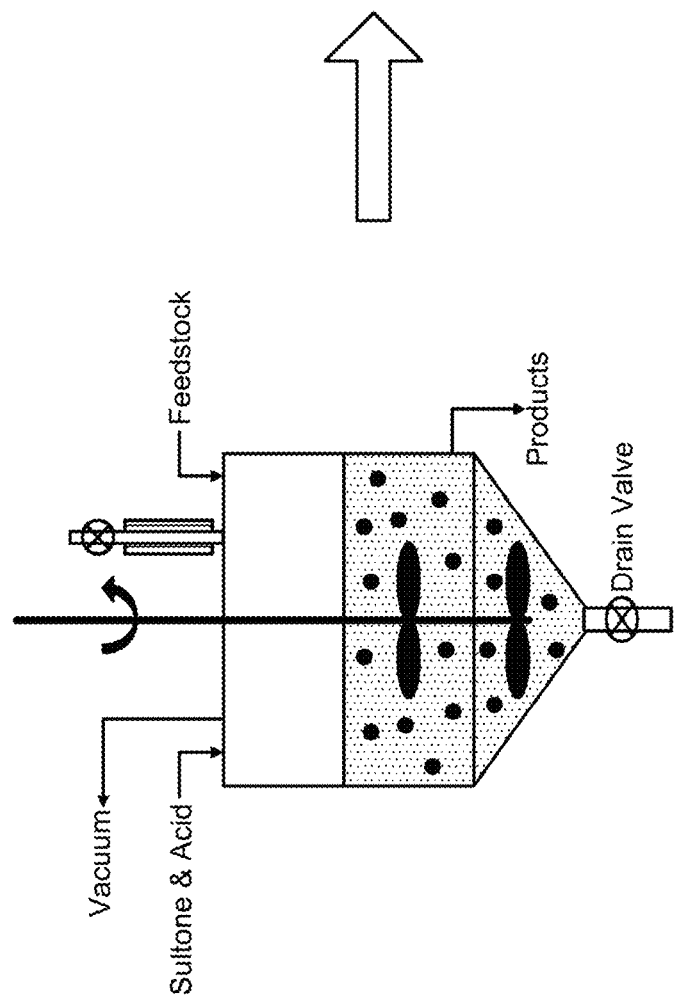
FIG. 3 is the view showing the transacylation and the stratification.
Figure 3:
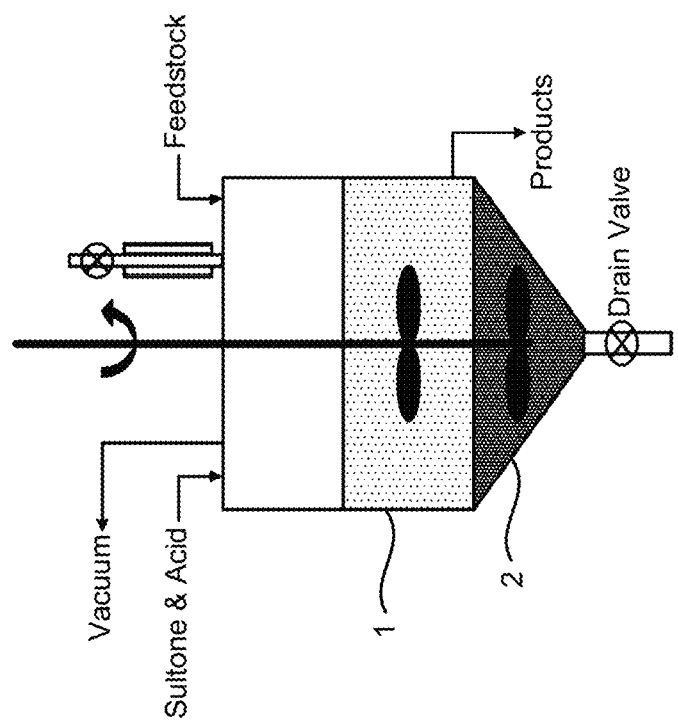

Please refer to FIG. 2 and FIG. 3, which are a view showing reactions of fabricating the IL; and a view showing transacylation and stratification. As shown in the figures, on using the present invention, for fabricating an acidic IL as a catalyst, pyridine or 1-butyl-imidazole (N-butyl imidazole) is reacted with 1,3-propane sultone at 40° C. for 24 hrs to obtain a white solid of a zwitterionic compound. After being purified with ether and dried through vacuuming, the white solid of the zwitterionic compound of $R^+$—$(CH_2)_3$—$SO_3$— is obtained, where R is pyridine or 1-butyl-imidazole (i.e. n-propane sulfonic acid pyridinium (PSPy) or pyridinium propyl sulfobetaine (PPS)). An appropriate amount of the white solid is obtained in a round bottom flask to be added with a considerable number of moles of sulfuric acid for reaction with stirring at 100° C. for 0.5 hr. A transparent viscous liquid is gradually formed, which is an acidic IL of $[R^+$—$(CH_2)_3$—$SO_3H][HSO_4]$ obtained through the reaction shown in FIG. 2.

On processing transacylation, soybean oil (i.e. TG) is obtained and a mixture of soybean oil and HOAc is poured into the viscous IL and reaction is processed under heating with stirring at a speed of 400 rounds per minute (rpm). After the reactions, the liquid is stratified into layers. The product 1 at upper layer is taken out to be analyzed through gas chromatograph (GC) for acquiring composition and further calculating a conversion rate of soybean oil and selectivity of the transacylated product. The reaction conditions include a temperature of 50~120° C. and a HOAc/TG mole ratio of 5~80. When sulfuric acid is used as the Bronsted strong acid, the IL obtained is a sulfated sulfonic-acid IL with a $IL(H_2SO_4)$/TG mole ratio of 1.0~1.5. When HPA is used as the Bronsted strong acid, the IL obtained is a HPA-ed sulfonic-acid IL with a IL(HPA)/TG mole ratio of 0.2~0.5. The reaction time is 1~72 hrs. Reusability of the IL is tested as follows: After the reaction is finished and layers are separated, the IL 2 is located at lower layer. Under 95° C., excess HOAc is expelled through vacuuming. Afterwards, a new feedstock can be added for process reaction repeatedly. Or, under heating, HOAc is recycled through vacuuming. After processing stratification by staying still, the IL at the lower layer can be fed with a new feedstock for reaction repeatedly, whose reactions are shown in FIG. 3. In the figure, the left part shows transacylation with the IL; and the right part shows stratification after taking out HOAc.

The following state-of-uses show feasibility and accuracy of the present invention.

[State-of-Use 1] Measurement of Transacylation Activity 2.0 g (0.01 mole) of PPS is uniformly mixed with 0.98 g (0.01 mole) of $H_2SO_4$ with stirring at 100° C. Then, 4 g (0.067 mole) of HOAc is added to form two layers of immiscible transparent liquids. The lower layer is a flowable IL. Then, 12 g (0.2 mole) of HOAc and 6.0 g (0.067 mole) of soybean oil (TG) are added with stirring at 100° C. continued for 24 hrs. After reactions, layers are not separated. The reaction flask is taken out from the oil bath and placed on a rotary evaporator for gradually removing HOAc by heating under a reduced pressure. Then, the liquid in the flask is separated into two layers by staying still. The upper layer contains clear fatty acids and transacylated products; and, the lower layer contains the flowable IL. The upper liquid is taken out to analyze the fatty acids and transacylated products contained within (TG, DG, MG, FFA, AFFA and GTA) for obtaining their molar ratios. When GTA has a higher mole % and TG has a lower mole %, it means a higher transacylation activity with the catalyst. Through GC, a soybean oil (TG) conversion of 97.9% is obtained. The mole % of TG, DG, MG, FFA, AFFA and GTA are 0.6%, 2.5%, 5.9%, 37.4%, 34.4% and 19.2%, respectively. Therein, the selective of the fatty acids (FFA+AFFA) is 71.8%.

[State-of-Use 2] Transacylation Activity Affected by Molar Ratio of HOAc/TG

As following the method used in the state-of-use 1, the mole ratio of HOAc/TG is changed to 20, 40, 60 and 80 for testing transacylation activity. Therein, the molar ratio of $PPS/H_2SO_4$ is 1.0 and the molar ratio of $IL(H_2SO_4)$/TG is 1.5 for reaction at 100° C. for 24 hrs. As shown in Table 1, the transacylation conversion rate of the IL is significantly improved as following the increase of the mole ratio of HOAc/TG. When the mole ratio is less than 20, stratification fails after removing HOAc. The selectivity of the fatty acids (FFA+AFFA) is improved from 68.6% for the mole ratio of 20 to 74.3% for the mole ratio of 80. Because excess HOAc needs to be recycled, a preferred mole ratio of HOAc/TG is 40~60.

TABLE 1

| | Reaction conditions | | | | Con-version (%) | Product composition (mole %) | | | | | |
|---|---|---|---|---|---|---|---|---|---|---|---|
| | HOAc/feed mole ratio | IL/feed mole ratio | Temp. (° C.) | Time (hr) | | TG | DG | MG | FFA | AFFA | GTA |
| TA-1 | 20/1 | 1.5/1 | 100 | 24 | 95.9 | 1.3 | 11.0 | 5.3 | 41.2 | 27.4 | 13.8 |
| TA-2 | 40/1 | 1.5/1 | 100 | 24 | 97.9 | 0.6 | 2.5 | 5.9 | 37.4 | 34.4 | 19.2 |
| TA-3 | 60/1 | 1.5/1 | 100 | 24 | 100 | 0 | 0 | 3.9 | 29.6 | 44.4 | 22.1 |
| TA-4 | 80/1 | 1.5/1 | 100 | 24 | 100 | 0 | 0 | 2.6 | 23.8 | 50.5 | 23.1 |

[State-of-Use 3] Transacylation Activity Affected by Amount of Acidic IL

As following the method used in the state-of-use 1, the molar ratio of PPS/$H_2SO_4$ is 1.0 and the amount of catalyst is changed. The molar ratio of IL($H_2SO_4$)/TG is changed to 0.5, 1.0, 1.5 and 2.0, respectively, for reaction at 100° C. for 24 hrs while HOAc/TG is 40. As shown in Table 2, the conversion rate of transacylation increases as following the increase of the acidic IL amount.

TABLE 2

| | Reaction conditions | | | | Con-version (%) | Product composition (mole %) | | | | | |
|---|---|---|---|---|---|---|---|---|---|---|---|
| | HOAc/feed mole ratio | IL/feed mole ratio | Temp. (° C.) | Time (hr) | | TG | DG | MG | FFA | AFFA | GTA |
| TA-5 | 40/1 | 2.0/1 | 100 | 24 | 100 | 0 | 1.9 | 5.5 | 29.1 | 43.6 | 19.9 |
| TA-2 | 40/1 | 1.5/1 | 100 | 24 | 97.9 | 0.6 | 2.5 | 5.9 | 37.4 | 34.4 | 19.2 |
| TA-6 | 40/1 | 1.0/1 | 100 | 24 | 96.9 | 0.9 | 3.8 | 7.4 | 39.5 | 31.1 | 17.3 |
| TA-7 | 40/1 | 0.5/1 | 100 | 24 | 96.1 | 1.2 | 5.5 | 8.4 | 41.5 | 27.7 | 15.7 |

[State-of-Use 4] Transacylation Activity Affected by Reaction Temperature and Reaction Time As following the method used in the state-of-use 1, the molar ratio of PPS/$H_2SO_4$ is 1.0, the molar ratio of IL($H_2SO_4$)/TG is 1.5 and HOAc/TG is 40. The reaction temperature and the reaction time are changed for processing transacylation. As shown in Table 3, transacylation activity increases as following the increase of the reaction temperature. The selectivity of the fatty acids (FFA+AFFA) increases from 68.8% at 80° C. to 74.0% at 120° C. Yet, since the boiling point of HOAc is 117° C., a preferred reaction temperature is 100~110° C. In addition, for reactions at 100° C., if the reaction time is more than 48 hrs, transacylation activity only slightly increases from 73.1% for 48 hrs to 73.4% for 72 hrs. Hence, a preferred reaction time is 24~48 hrs.

[State-of-Use 5] Transacylation Activity with Tungsto-Phosphoric Acid (TPA) as Catalyst As following the method used in the state-of-use 1, TPA is obtained to replace $H_2SO_4$ for reactions under conditions of a PPS/TPA mole ratio of 2/1, HOAc/TG of 40/1, the amount of IL(TPA)/TG catalyst of 0.2/1, a reaction temperature of 100° C. and a reaction time of 48 hrs. The result is a TG conversion rate of 100%; the mole % of the product DG, MG, FFA, AFFA GTA are 1.3%, 4.0%, 29.3%, 44.0% and 21.3%, respectively. It shows that TPA can be used for the IL to effectively process transacylation and addition acetoxylation. Therein, the selectivity of the fatty acids (FFA+AFFA) reaches 73.3%; the selectivity of GTA is 21.3%, which is a similar transacylation activity than $H_2SO_4$.

[State-of-Use 6] Catalyst Reusability

As following the method used in the state-of-use 1, the molar ratio of PPS/$H_2SO_4$ is 1.0, the molar ratio of IL($H_2SO_4$)/TG is 1.5 and HOAc/TG is 40. The reactions are processed at 100° C. for 48 hrs. After the reactions, a rotation evaporator is used for heating under a reduced pressure to remove excess HOAc. After processing stratification by staying still, the product at upper layer is taken out with the IL left in the reaction flask. A new reaction solution is added to process the reactions under the same conditions. The

TABLE 3

| | Reaction conditions | | | | Con-version (%) | Product composition (mole %) | | | | | |
|---|---|---|---|---|---|---|---|---|---|---|---|
| | HOAc/feed mole ratio | IL/feed mole ratio | Temp. (° C.) | Time (hr) | | TG | DG | MG | FFA | AFFA | GTA |
| TA-8 | 40/1 | 1.5/1 | 120 | 48 | 100 | 0 | 0.5 | 3.1 | 23.7 | 50.3 | 22.4 |
| TA-9 | 40/1 | 1.5/1 | 100 | 48 | 98.5 | 0.4 | 1.3 | 4.0 | 32.2 | 40.9 | 21.2 |
| TA-10 | 40/1 | 1.5/1 | 80 | 48 | 96.2 | 1.2 | 8.1 | 5.0 | 41.3 | 27.5 | 16.9 |
| TA-11 | 40/1 | 1.5/1 | 100 | 16 | 97.0 | 0.9 | 5.4 | 5.6 | 42.1 | 28.1 | 17.9 |
| TA-2 | 40/1 | 1.5/1 | 100 | 24 | 97.9 | 0.6 | 2.5 | 5.9 | 37.4 | 34.5 | 19.1 |
| TA-12 | 40/1 | 1.5/1 | 100 | 72 | 100 | 0 | 1.1 | 4.0 | 26.4 | 47.0 | 21.5 | whole processes are operated two times (i.e. TA-9a and TA-9b). As the results shown in Table 4, the catalyst of the acidic IL can be recycled without significant activity decay.

TABLE 4

|  | Reaction conditions | | | Con- | Product composition | | | | | |
| --- | --- | --- | --- | --- | --- | --- | --- | --- | --- | --- |
|  | HOAc/feed | IL/feed | Temp. | Time | version | (mole %) | | | | |
|  | mole ratio | mole ratio | (° C.) | (hr) | (%) | TG | DG | MG | FFA | AFFA | GTA |
| TA-9 | 40/1 | 1.5/1 | 100 | 48 | 98.5 | 0.4 | 1.3 | 4.0 | 32.2 | 40.9 | 21.2 |
| TA-9a | 40/1 | 1.5/1 | 100 | 48 | 98.1 | 0.5 | 1.4 | 4.0 | 35.1 | 38.1 | 20.9 |
| TA-9b | 40/1 | 1.5/1 | 100 | 48 | 97.1 | 0.8 | 1.6 | 4.3 | 34.8 | 37.8 | 20.7 |

The water-based acidic IL reacts with a traditional liquid acid and a specific organic nitrogen-containing compound to generate an IL having almost no vapor pressure. After the reactions, the product and the IL acidic catalyst are stratified, so that there is no waste acid left to be dealt with. Therein, for fabricating the Bronsted acidic IL, an organic nitrogen-containing compound is reacted with alkyl sultone at first to generate a white solid of a zwitterionic compound. After processing purification, a liquid acid ($H_2SO_4$, $CF_3SO_3H$, p-$CH_3$—$C_6H_4$—$SO_3H$ or HPA) is obtained for reaction to generate a highly viscous transparency of a Bronsted acidic IL. Thus, the present invention stratifies the product and the strong acidic catalyst for recycling the catalyst so that problems of product stratification, waste acid treatment and equipment corrosion are solved. The yield of products generated through transacylation and addition acetoxylation is improved through such green catalytic processes.

To sum up, the present invention is a method of fabricating fatty acids through transacylation, where, by using a water-based acidic IL as a catalyst, an oil is processed through transacylation and addition acetoxylation to generate AFFA and GTA; problems of product stratification, waste acid treatment and equipment corrosion are solved; and the yield of products generated through transacylation and addition acetoxylation is improved through such green catalytic processes.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method of fabricating fatty acids through transacylation, comprising steps of:
   (a) reacting an organic nitrogen-containing compound with an alkyl sultone to obtain a white solid of a zwitterionic compound; after being purified and dried, obtaining a powder of said white solid to be reacted with a Bronsted strong acid in acetic acid (HOAc) to obtain a clear viscous water-based acidic ionic liquid (IL),
      wherein a mole ratio of said Bronsted strong acid to said zwitterionic compound is 1.0~3.0;
   (b) adding a mixture of an oil (triglyceride, TG) and HOAc in said IL; using said oil and HOAc as a reactant feedstock and said IL as a catalyst to process transacylation and addition acetoxylation under reaction conditions of a temperature of 50~150 celsius degrees (° C.) and a reaction time of 1~72 hours (hr),
      wherein a molar ratio of said IL to said oil is 0.2~2.0 and a molar ratio of HOAc to said oil (HOAc/TG) in said reactant feedstock is 5~80; and
   (c) after reactions, recycling HOAc through vacuuming by heating under a reduced pressure; stratifying a product and said IL by staying still; taking out said product at upper layer and leaving said IL at lower layer to be recycled to repeatedly process transacylation and addition acetoxylation with said reactant feedstock added; and obtaining fatty acids, including a stabilized acetoxy fatty acid (AFFA), from said product at upper layer after taking out glycerol triacetate (GTA) through vacuum distillation.

2. The method according to claim 1,
   wherein said organic nitrogen-containing compound is selected from a group consist of an alkylimidazole, an alkylpyridine and an alkylamine.

3. The method according to claim 2,
   wherein said organic nitrogen-containing compound has an alkyl group of $C_mH_{2m+1}$, and m is 1~18.

4. The method according to claim 1,
   wherein said alkyl sultone has an alkyl group of $C_nH_{2n}$, and n is 3~6.

5. The method according to claim 1,
   wherein said Bronsted strong acid is selected from a group consist of sulfuric acid ($H_2SO_4$), an alkyl sulfonic acid (R—$SO_3H$) and heteropoly acid (HPA).

6. The method according to claim 5,
   wherein said alkyl sulfonic acid is selected from a group consist of fluorosulfuric acid ($FSO_3H$, FS), trifluoromethane sulfonic acid ($CF_3SO_3H$, TFMSA) and p-toluenesulfonic acid (p-$CH_3$—$C_6H_4$—$SO_3H$, P-TSA).

7. The method according to claim 5,
   wherein said HPA is selected from a group consist of phosphotungstic acid ($H_3PW_{12}O_{40}$), phosphomolybdic acid ($H_3PMo_{12}O_{40}$), silicotungstic acid ($H_4SiW_{12}O_{40}$) and silicomolybdic acid ($H_4SiMO_{12}O_{40}$).

8. The method according to claim 7,
   wherein said HPA is calcined at a temperature of 100~500° C. to remove crystal water.

9. The method according to claim 1,
   wherein said Bronsted acid is sulfuric acid or alkyl sulfonic acid; and
   wherein a molar ratio of said IL to TG is 1.0~1.5.

10. The method according to claim 1,
    wherein said Bronsted acid is an HPA; and
    wherein a molar ratio of said IL to TG is 0.2~0.5.

11. The method according to claim 1,
    wherein a molar ratio of HOAc to said oil in said reactant feedstock is 40~60.

12. The method according to claim 1,
    wherein said transacylation is processed under conditions of a reaction temperature of 100~110° C. and a reaction time of 24~48 hrs.

13. The method according to claim 1,
wherein said oil is selected from a group consist of a waste edible oil, an epoxy oil and an energy crop oil.

14. The method according to claim 13,
wherein said energy crop oil is a non-edible oil selected from a group consist of jatropha oil, castor oil, high-acid algae oil and pongamia oil.

* * * * *